(12) United States Patent
Herrera

(10) Patent No.: US 6,899,695 B2
(45) Date of Patent: May 31, 2005

(54) MEDICATION SECURITY APPARATUS AND METHOD

(76) Inventor: Hector J. Herrera, 2233 Chilton Rd., Houston, TX (US) 77019

( * ) Notice: Subject to any disclaimer, the term of this patent is extended or adjusted under 35 U.S.C. 154(b) by 0 days.

(21) Appl. No.: 10/637,606

(22) Filed: Aug. 8, 2003

(65) Prior Publication Data

US 2005/0033223 A1 Feb. 10, 2005

(51) Int. Cl.[7] ............................................. A61M 31/00
(52) U.S. Cl. ........................................................ 604/65
(58) Field of Search ................................. 604/131, 132, 604/65, 66, 67, 151, 133–136, 140, 150, 154, 156, 246, 247, 118, 121

(56) References Cited

U.S. PATENT DOCUMENTS

| | | | |
|---|---|---|---|
| 5,047,009 A | 9/1991 | Morris | |
| 5,069,668 A | 12/1991 | Boydman | |
| 5,345,538 A | 9/1994 | Narayannan | |
| 5,713,856 A | 2/1998 | Eggers | |
| 5,848,988 A | 12/1998 | Davis | |
| 6,010,483 A | 1/2000 | Spencer | |
| 6,135,949 A | 10/2000 | Russo et al. | |
| 6,231,560 B1 | 5/2001 | Bui et al. | |
| 6,241,704 B1 | 6/2001 | Peterson | |
| 6,278,975 B1 | 8/2001 | Brant et al. | |
| 6,355,018 B1 | 3/2002 | Vasko | |
| 6,554,798 B1 * | 4/2003 | Mann et al. | ................. 604/131 |
| 6,577,899 B2 * | 6/2003 | Lebel et al. | .................. 607/60 |
| 6,641,533 B2 * | 11/2003 | Causey et al. | .............. 600/300 |
| 6,780,156 B2 * | 8/2004 | Haueter et al. | ............. 600/459 |
| 6,786,885 B2 * | 9/2004 | Hochman et al. | ............. 604/67 |

* cited by examiner

*Primary Examiner*—Manuel Mendez
(74) *Attorney, Agent, or Firm*—Tim L. Burgess, P.C.

(57) ABSTRACT

A security device for a patient-controlled analgesia (PCA) device receives a word or series of words spoken into it as a command by a patient and creates a voice print characteristic of the patient. A subsequent receipt of a voiced command is converted into a test voice print and compared to the patient's voice print. If the system identifies the test voice print as belonging to the patient's voice, it signals the PCA that the patient is requesting a bolus of medication from the PCA. If the device determines that the test voice print does not correspond to that of the patient, the device does not signal the PCA and optionally emits an audible error tone. In this manner, unauthorized people cannot give the patient a bolus dose from the PCA.

12 Claims, 5 Drawing Sheets

MEDICATION SECURITY APPARATUS AND METHOD

BACKGROUND OF THE INVENTION

This invention relates to infusion pumps for delivery of medication to patients, and more particularly to patient controlled analgesic pumps in which the patient commands the infusion pump to deliver the analgesic by pressing a switch at a distal end of a cable connected to the pump controller.

Infusion pumps for delivering pain medications have been on the market for many years. Typically, a patient has one of these devices to control pain post operatively. In use, the physician will set up the device near the patient's bedside and program the instrument to deliver analgesics over time. Typically, there will be a cable attached to the device with a button on the distal end and clipped to the patient's bed. In this manner the patient may press the button to give a bolus of pain reliever if needed to manage pain. Safeguards are built into the system as to how often the patient may deliver pain medication so that the patient doesn't overdose.

A difficulty arises in the lack of security for such systems, in that they permit the administration of analgesics by command of others than the patient or professional caregivers at the care facility. Family members, anxious about a loved one's pain, unwittingly may command the pump to administer more analgesic than the patient needs or wants, or at times when the patient is unconscious, or without the knowledge or consent of the patient, endangering the patient. There is the risk too of the malevolent person who may intend to overdose the patient.

A need exists to permit a patient to deliver pain medication as needed, within the dosing parameters set up in the infusion pump by caregivers, while not allowing the medication delivery equipment to be commanded by other persons.

This invention is directed to that need, and supplies either an add-on to existing patient commanded medication delivery devices or an integrated patient commanded medication delivery apparatus, in either case, in which only the patient can command delivery of the medication on an as needed or wanted basis.

SUMMARY OF THE INVENTION

The present invention uses a voice sound recognition algorithm which creates a voice print that distinguishes the patient's voice command from other voices which would speak the same command, in order to ensure that only the patient controls the bolus dose to himself or herself. It is important to distinguish voice sound from speech-recognition, which is generally used to recognize and distinguish between differing word sounds in a vocabulary of words, in order to perform a task commanded by the vocabulary. In the present invention, voice prints are made from voiced word sounds and are used to discriminate between the command word or words sound made by the patient and the same command word or words sound made by anyone other than the patient, and to allow the task to be performed only if the patient is attempting the activation.

The invention includes a method of dispensing a dosage of medication on voice command discriminated to be solely that of the patient, and as well includes apparatus for dispensing a dosage of medication on voice command of solely the patient. The apparatus may be either a totally integrated medication system using a single microprocessor or may be an add-on module to an existing patient controlled infusion device.

In accordance with the method of the invention, a dosage of medication is dispensed from a medication reservoir to a patient on voice command of the patient. The patient is fluidly connected to a medication delivery line from a pump operatively connected to a reservoir of the medication. A prescribed medication regime containing limits of dosage administration is set and locked into a microprocessor. The microprocessor is capable of commanding the pump to pump a single dose of the medication upon receipt of such command. A voice sound from the patient is converted into an electrical signal representing a first voice pattern. The voice pattern is received and processed in the microprocessor upon connection of the electrical signal to the processor, to analyze the first voice pattern and produce digital data representing a first voice print of the patient. The data is transferred to digital memory storage associated with the processor. A subsequent voice sound from a voice source is converted into a second electrical signal representing a test voice pattern. The test voice pattern is received and processed in the microprocessor to analyze the test voice pattern and produce digital data representing a test voice print. The data representing the patient's voice print is retrieved from memory storage. The test voice print is compared to the first voice print by the microprocessor to determine whether the test voice print is a match for the patient's voice print, and if there is a match, the microprocessor commands the pump to dispense a single dose of the medication if a limiting parameter of the medication regime is not exceeded.

The invention comprises a security device for a patient-controlled analgesia (PCA) device receives a word or series of words spoken into it as a command by a patient and creates a voice print characteristic of the patient. A subsequent receipt of a voiced command is converted into a test voice print and compared to the patient's voice print. If the system identifies the test voice print as belonging to the patient's voice, it signals the PCA that the patient is requesting a bolus of medication from the PCA. If the device determines that the test voice print does not correspond to that of the patient, the device does not signal the PCA and optionally emits an audible error tone. In this manner, unauthorized people cannot give the patient a bolus dose from the PCA.

Thus the invention includes a module for operative connection with an existing patient controlled medication device to prevent unauthorized use of the device to medicate the patient. The existing device includes a microprocessor programmable by an authorized operator to set and lock a dosage of medication regime for a patient, a reservoir for a fluid medication, and a pump operatively associated with the reservoir and operatively connected to the microprocessor for pumping fluid from the reservoir on command from the microprocessor. The module connectable to the existing device comprises a microphone for receiving voice sound from a voice source and converting it to an electrical signal representative of the voice pattern of the voice source. The microphone is in electric communication with a digital signal processor with associated digital memory storage. The processor has capability for receiving and analyzing an electrical signal from the microphone to produce digital data representing a learned voice print of a voice source and for transferring the data to and from the memory storage. Upon receipt of an electrical signal from the microphone subsequent to having committed a learned voice print to memory storage, the digital signal processor has capability for producing a test voice print representing the subsequent signal from a voice source, for retrieving the learned and stored voice print and determining whether a match exists between the two voice prints, and if so, for issuing an electrical command to the microprocessor to examine the medical regime to determine whether to instruct the pump to discharge a dosage of the medication. A source of power is provided for operating the digital signal processor. Suitably a switch is operable by the patient for activating the digital signal processor. The switch operable by a patient may switch closed a normally open electrical circuit connecting a source of electrical power to the digital signal processor. Suitably also, the digital signal processor is switchable to a "learn" position by a switch secured from access by other than an authorized operator. Switching the switch to the learn position erases any voice print in the data storage and enables the digital signal processor to receive and analyze an electrical signal representing the voice pattern of the patient to produce digital data representing a learned voice print. An annunciator is electrically connected to the digital signal processor for announcing a condition of the digital signal processor.

Also in accordance with the invention, an integrated patient controlled fluid medication security apparatus is provided. The integrated apparatus comprises a reservoir for a fluid medication and a pump operatively associated with the reservoir for pumping fluid from the reservoir on command. A microprocessor of the apparatus is programmable by an authorized operator to set and lock a dosage of medication regime for a patient, the microprocessor having associated digital memory storage. The microprocessor is in electrical communication with a microphone that can receive voice sound from a voice source and convert the voice sound into an electrical signal representative of the voice pattern of the voice source. The microprocessor has capability for receiving and analyzing an electrical signal from the microphone, to produce digital data representing a learned voice print of a voice source and for transferring the data to and from the storage, and upon receipt of an electrical signal from the microphone subsequent to having committed a learned voice print to memory storage, the microprocessor has capability for producing a test voice print representing the subsequent signal from a voice source, for retrieving the learned voice print from storage and determining whether a sufficient match exists between the learned voice print and the test voice print, and if so, for examining the programmed medication regime to determine whether to instruct the pump to discharge a dosage of the medication. A source of electrical power is provided for operating the microprocessor. Suitably a switch is operable by a patient for activating the microprocessor. The switch operable by the patient may switch to closed position a normally open electrical circuit connecting a source of electrical power to the microprocessor. Suitably, the microprocessor is switchable to a "learn" position by a switch secured from access by other than an authorized operator. Switching the switch to the learn position operates to erase any voice print in the data storage associated with the microprocessor and enables the microprocessor to receive and analyze an electrical signal representing the current patient's voice pattern, to produce digital data representing a learned voice print of the patient. Also, suitably, an annunciator is electrically connected to the microprocessor for announcing a condition of the processor, such as a ready to learn position or other condition announced by the processor.

DETAILED DESCRIPTION OF THE INVENTION

Figure 1:
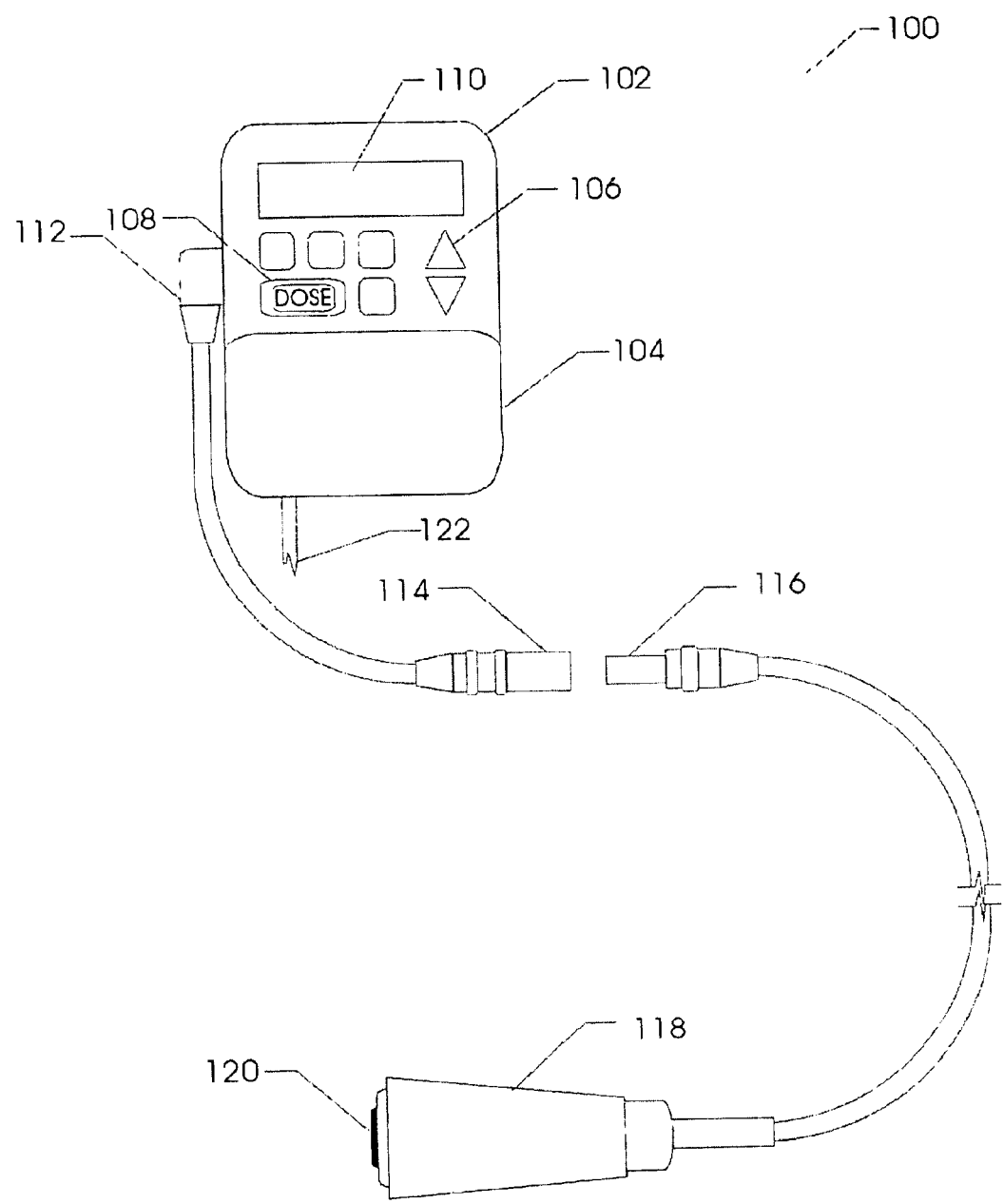
FIG. 1 is a drawing of a conventional patient-controlled analgesia ("PCA") device with a remote dose cord/button.

FIG. 1 depicts a conventional PCA device with a remote/cord button 100. The housing contains the analgesic container 104 and the electronics and pump portion 102. In the electronics part 102 of the device there are scroll keys 106 and a keyboard keys 108 including a "dose" key, and a display 110 which is a liquid crystal display ("LCD"). In use, the clinician will program the device using a combination of the function keys 108 and scroll keys 106 while monitoring the LCD 110. Once the desired frequency and volume of the analgesic is set the unit is "locked" by activating a software locking feature. The PCA is typically mounted behind the patient's bed on a wheeled pole which permits the patient to walk with the PCA as desired. The remote dose feature is comprised of a connector 112 that plugs into the electronic portion 102 of the device and terminates into a connector 114. A mating connector 116 may be plugged into it and consists of a length of cable terminating in a housing 118 in which a switch 120 resides. This switch housing 118 frequently has a clip on it to attach switch housing 118 to the patient's bed for easy access. When authorized, after the clinician has programmed the PCA 100, the patient may push button 120. Upon doing so, the electronics in housing 102 dispense a controlled amount of analgesic from the container 104, to the patient via a catheter 122.

Figure 2:
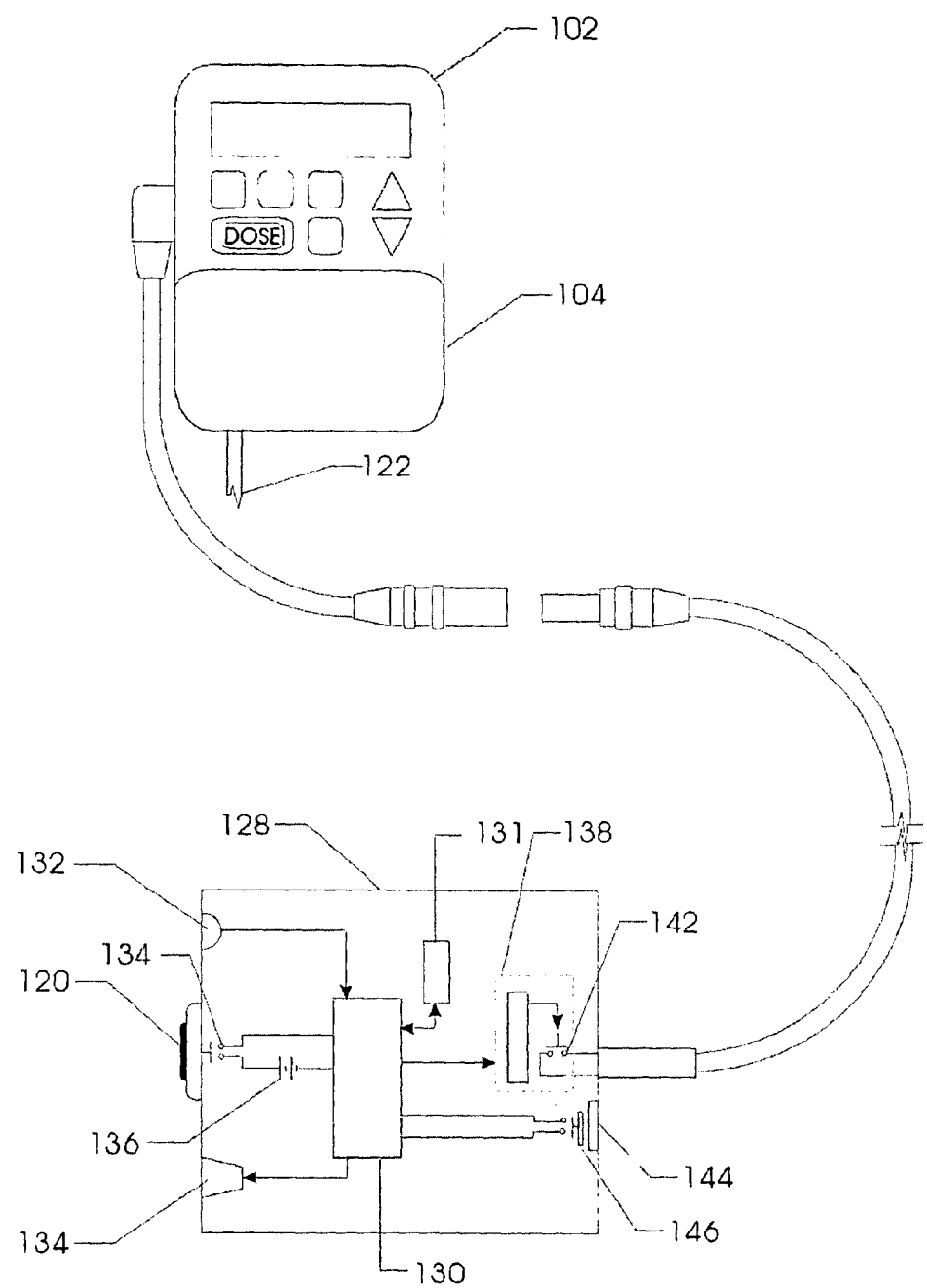
FIG. 2 is a drawing of a PCA with a remote dose cord/button with voice interlock schematic.

FIG. 2 illustrates a preferred embodiment of the present invention comprising a module for operative connection with an existing patient controlled medication device such as the device exemplified in FIG. 1. The switch housing 118 in FIG. 1 is now represented by 128 in FIG. 2, which houses the button 120 plus additional electronics. These electronics comprise digital signal processor 130, a microphone 132, an annunciator 134, and an electronic switch 138. The signal processor 130 is operatively associated with a digital storage component, such as a flash memory, indicated at 131, which memory may be external (as shown) or internal. In use, the patient depresses the normally open switch 120 and closes the contacts 134 which completes the circuit and connects the battery 136 that powers the circuitry. At this time the patient speaks a particular word or set of words, which should be more than one syllable, into the microphone 132. The digital signal processing unit 130 compares the patient's pattern of speech with the stored pattern or patterns of the same patient. If the patterns match, then the device 130 commands an electronic switch 138 to close the contacts 142. This closure then allows current flow to the electronics portion 106 of the PCA. At the same time the annunciator 134 "beeps" or makes an appropriate auditory tone to let the patient know that the process has been completed and the patient can release button 120. Once the patient releases the hold on button 120 the circuitry in housing 128 powers down as the circuit is now open. The PCA determines whether the programmed parameters are appropriate to medicate the patient after receiving the closure signal from switch 142. If so, then medication from the reservoir 104 is delivered to the patient via catheter 122.

To program the unit with the patient's voice pattern, access port 144 on housing 128 is removed by a clinician by key or other mechanism to expose switch 146. This switch is moved to its other position. The clinician then depresses switch 120 to energize the unit. The processing system 130 determines that switch 146 is in its alternate position and so enters the "learning" mode. In this mode the processing unit 130 erases it's stored voice patterns and an annunciator 134 signals by beeping three times, as an example, to indicate to the clinician that the unit us ready for programming. The clinician holds the unit up to the patient who says a predetermined phrase into the microphone. The system may, via the annunciator, indicate adequate capture of information and then beep three times again to capture a second sample from the patient. Capturing more than one voice pattern sample permits the processor 130 to undertake some averaging of the voice pattern which will permit it to accept wider variation of the patient's voice print and, ultimately, better discrimination against non-patient voice inputs. Alternatively, the processing system may use the second voice print of the patient to compare with the first voice print. Once finished, the annunciator will beep a series of times to indicate successful acquisition of the desired number and/or validation of the voice prints. The clinician can then release button 120 and move switch 146 back to it's original position and close the access port 144. It should be noted that if 144 were a keyway and the clinician used a key to move from "close" to "open" and if switch 146 engaged in the "open" position then access port 144 is not necessary.

Figure 3:
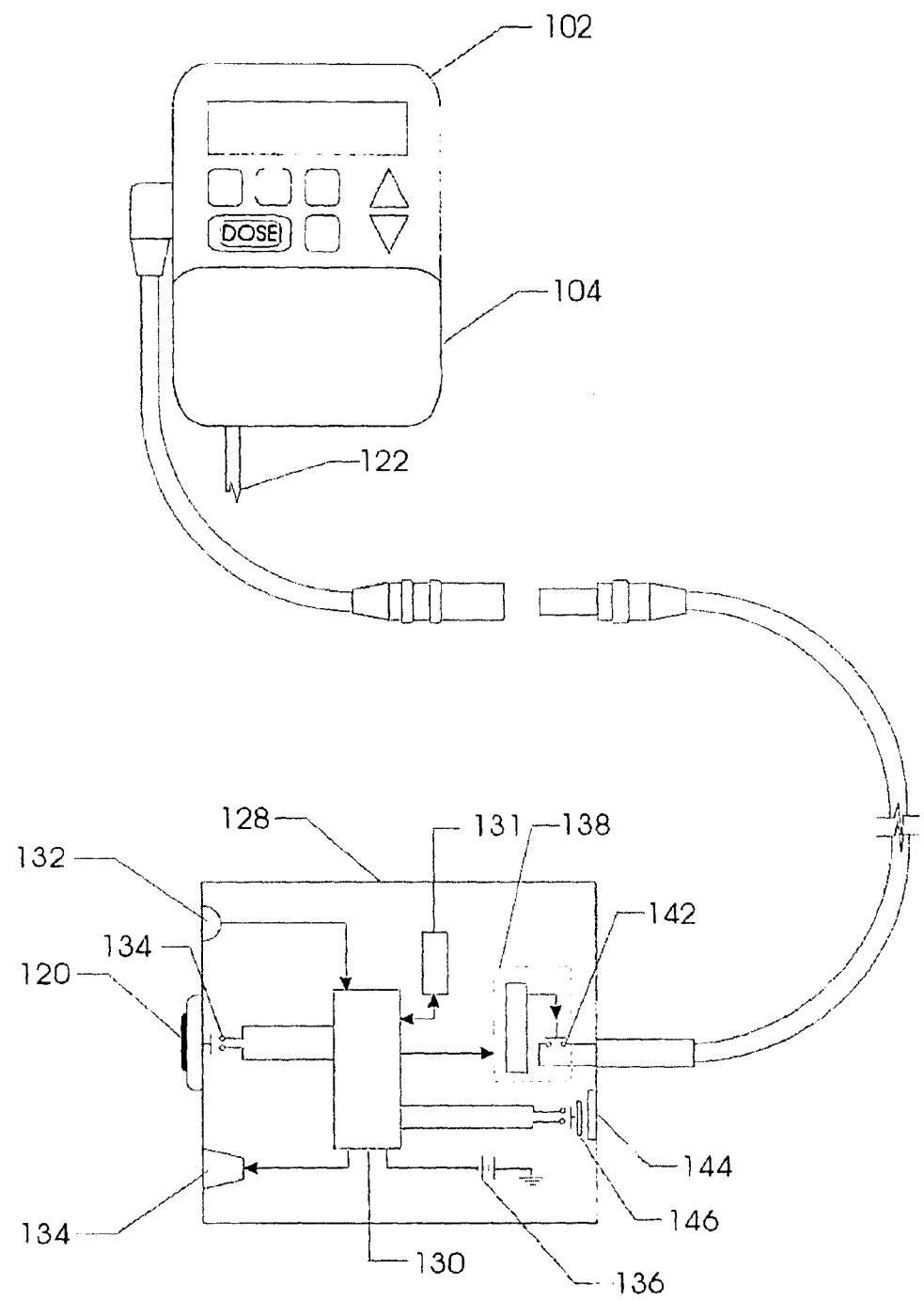
FIG. 3 is a drawing with another embodiment of the PCA with a remote dose cord/button with a voice interlock schematic.

FIG. 3 illustrates another embodiment of the present invention. It is similar to the embodiment shown in FIG. 2 except the battery is moved out of the contact circuitry of the switch 120. In this embodiment power is always available and the processing system 130 is in a "sleep" mode, drawing very little current. When button 120 is pushed, it closes the circuit as before. In this embodiment the processor 130 "wakes up" and performs all of the functions described earlier. The benefit of this embodiment is that the patient can push the button 120 momentarily and not have to hold the button closed throughout the entire speaking process. In "learning" mode, button 120 also only has to be pushed momentarily. The disadvantage of this approach is that battery life will be shorter.

Figure 4A:
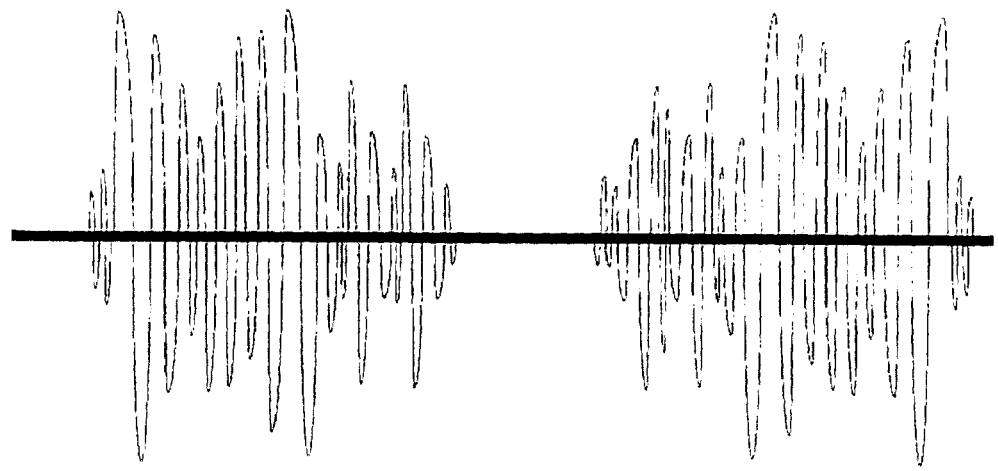
FIG. 4 is a drawing showing the steps of digitizing a voice print.
Figure 4B:
Figure 4C:
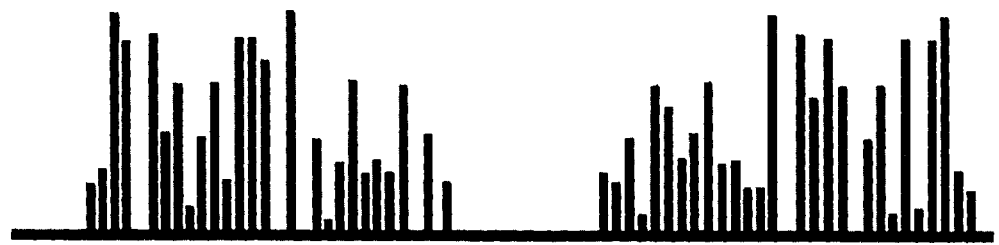

FIG. 4 illustrates one embodiment of capturing voice prints. FIG. 4A illustrates an intensity vs. time plot of two single-syllable words. During processing of this data the processing system 130 will eliminate all of the data below zero leaving the data as illustrated in FIG. 4B. Digitizing the data will leave digital data values, as graphically represented in FIG. 4C. Inside the system this will simply be a series of stored numbers.

Figure 5:
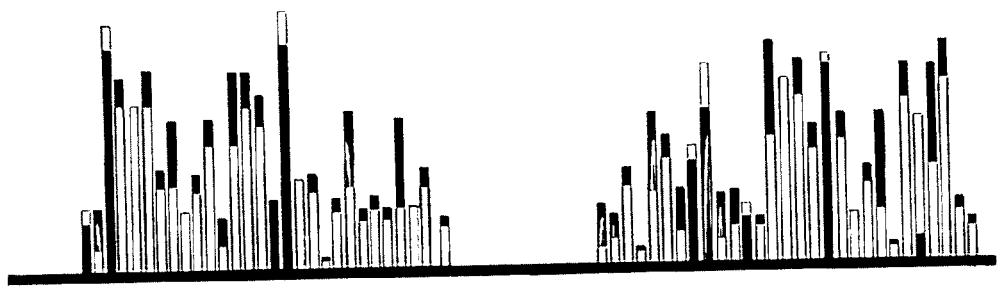
FIG. 5 is a drawing showing the comparison of two dissimilar voice prints.

FIG. 5 illustrates the superimposition of someone else saying the same words (in white) over the original voice print (in black). The technique or comparing these values these data values in memory is commonly known by those skilled in the art. In practice, the voice print from the patient is compared to the stored value of the patient and the algorithm attempts to align the two along the time axis. If a sufficient match is made the system closes switch 142. If not then switch 142 is left open and the annunciator beeps an error.

While certain advantageous embodiments have been chosen to illustrate the invention, it will be understood by those skilled in the art that various changes and modifications can be made herein without departing from the scope of the invention as defined in the appended claims.

What is claimed is:

1. A patient controlled fluid medication security apparatus, comprising:
    a) a reservoir for a fluid medication,
    b) a pump operatively associated with said reservoir for pumping fluid from said reservoir on command,
    c) a microphone for receiving voice sound from a voice source and converting it to an electrical signal representative of the voice pattern of the voice source,
    d) a programmable microprocessor programmable by an authorized operator to set and lock a dosage of medication regime for a patient,
    e) digital memory storage operatively associated with said microprocessor and in electrical communication with said microphone,
    f) a program of instructions for said microprocessor for causing said microprocessor to receive and analyze an electrical signal from said microphone, to produce digital data representing a learned voice print of a voice source, to transfer said data to said storage, and to cause said microprocessor, upon receipt of an electrical signal from said microphone subsequent to having committed a learned voice print to memory storage, to produce a test voice print representing the subsequent signal from a voice source, to retrieve said learned voice print from storage and to determine whether a sufficient match exists between the learned voice print and the test voice print, and if so, to examine the programmed medication regime to determine whether to instruct the pump to discharge a dosage of said medication, and
    g) a source of electrical power for operating said microprocessor.

2. The apparatus of claim 1 further comprising a switch operable by a patient for activating said microprocessor.

3. The apparatus of claim 1 further comprising a switch operable by a patient for switching closed a normally open electrical circuit connecting a source of electrical power to said microprocessor.

4. The apparatus of claim 1 in which said microprocessor is switchable to a learn position by a switch secured from access other than by an authorized operator, switching said switch to said learn position operating to erase any voice print in said data storage and enable said microprocessor to receive and analyze a said electrical signal to produce digital data representing a learned voice print.

5. The apparatus of claim 1 in which an annunciator is electrically connected to said microprocessor for announcing a condition of the microprocessor.

6. The apparatus of claim 1 further comprising a switch operable by a patient for activating said digital signal processor.

7. The apparatus of claim 1 in which said digital signal processor is switchable to a learn position by a switch secured from access other than by an authorized operator, switching said switch to said learn position operating to erase any voice print in said data storage and enable said digital signal processor to receive and analyze a said electrical signal to produce digital data representing a learned voice print.

8. The apparatus of claim 1 in which an annunciator is electrically connected to said digital signal processor for announcing a condition of the digital signal processor.

9. A module for connection with a patient controlled medication device to prevent unauthorized use of the device to medicate the patient, such device including a microprocessor programmable by an authorized operator to set and lock a dosage of medication regime for a patient, a reservoir for a fluid medication, and a pump operatively associated with said reservoir and operatively connected to said microprocessor for pumping fluid from said reservoir on command from said microprocessor, such module comprising:

a) a microphone for receiving voice sound from a voice source and converting it to an electrical signal representative of the voice pattern of the voice source, b) a digital signal processor with associated digital memory storage and being electrically connectable to said microphone, a program of instructions for said processor for causing said microprocessor to receive and analyze a connected said electrical signal from said microphone, to produce digital data representing a learned voice print of a voice source, to transfer said data to said storage, and to cause said microprocessor, upon receipt of an electrical signal from said microphone subsequent to having committed a learned voice print to memory storage, to produce a voice print representing the subsequent signal from a voice source, to retrieve said learned and stored voice print from storage and to determine whether a sufficient match exists between the two voice prints, and if so, to issue an electrical command to said microprocessor to examine the medical regime to determine whether to instruct the pump to discharge a dosage of said medication, and c) a source of power for operating said digital signal processor.

10. The apparatus of claim 9 further comprising a switch operable by a patient for switching closed a normally open electrical circuit connecting a source of electrical power to said digital signal processor.

11. A module for connection with a patient controlled medication device to prevent unauthorized use of the device to medicate the patient, such device including a microprocessor programmable by an authorized operator to set and lock a dosage of medication regime for a patient, a reservoir for a fluid medication, and a pump operatively associated with said reservoir and operatively connected to said microprocessor for pumping fluid from said reservoir on command from said microprocessor, such module comprising:

a) a microphone for receiving voice sound from a voice source and converting it to an electrical signal representative of the voice pattern of the voice source, b) a digital signal processor with associated digital memory storage and being electrically connectable to said microphone, a program of instructions for said processor for causing said processor to receive and analyze a connected said electrical signal from said microphone, to produce digital data representing a learned voice print of a voice source, to transfer said data to said storage, and upon receipt of an electrical signal from said microphone subsequent to having committed a learned voice print to memory storage, to produce a voice print representing the subsequent signal from a voice source, to retrieve said learned and stored voice print and determine whether a sufficient match exists between the two voice prints, and if so, to issue an electrical command to said microprocessor to examine the medical regime to determine whether to instruct the pump to discharge a dosage of said medication, said digital signal processor being switchable to a learn position by a switch secured from access other than by an authorized operator, switching said switch to said learn position operating to erase any voice print in said data storage and enable said digital signal processor to receive and analyze a said electrical signal to produce digital data representing a learned voice print, c) an annunciator electrically connected to said digital signal processor for announcing a condition of the digital signal processor, d) a source of power for operating said digital signal processor, and e) a switch operable by a patient for switching closed a normally open electrical circuit connecting a source of electrical power to said digital signal processor.

12. A method of dispensing a dosage of medication from a medication reservoir to a patient on voice command of the patient, comprising:

a) setting and locking a prescribed medication regime containing limits dosage administration within a least one time period into a microprocessor capable of commanding a pump operatively connected to a reservoir of the medication to pump a single dose of the medication upon receipt of such command, b) fluidly connecting a medication delivery line from said pump into a patient, c) converting a voice sound from the patient into an electrical signal representing a first voice pattern, d) receiving and processing said voice pattern in said processor upon connection of said electrical signal to said processor, to analyze said first voice pattern and produce digital data representing a first voice print of the patient, e) transferring said data to digital memory storage associated with said processor, f) converting a subsequent voice sound from a voice source into a second electrical signal representing a second voice pattern, g) receiving and processing said second voice pattern in said processor to analyze said second voice pattern and produce digital data representing a second voice print, h) retrieving said data representing said first voice print from said storage, i) comparing said second voice print to said first voice print in said processor to determine whether the second voice print is a match for the first voice print, and if there is a match, commanding the pump to dispense a single dose of the medication if a limiting parameter of said medication regime is not exceeded.

* * * * *